United States Patent [19]
Lichtenberg

[11] Patent Number: 5,725,501
[45] Date of Patent: Mar. 10, 1998

[54] SAFETY SYRINGE SYSTEM

[76] Inventor: Edward Lichtenberg, 2401 Pennsylvania Ave., Apt. 18 B27, Philadelphia, Pa. 19130

[21] Appl. No.: 775,971

[22] Filed: Jan. 3, 1997

[51] Int. Cl.[6] .................................................. A61M 5/00
[52] U.S. Cl. ........................................ 604/110; 604/243
[58] Field of Search ................................. 604/110, 240, 604/242, 243, 187, 272, 195, 218

[56] References Cited

U.S. PATENT DOCUMENTS

| | | | |
|---|---|---|---|
| 3,648,695 | 3/1972 | Bowen | 604/243 X |
| 4,950,253 | 8/1990 | Jacobs | 604/240 X |
| 5,201,716 | 4/1993 | Richard | 604/243 X |
| 5,246,423 | 9/1993 | Farkas | 604/110 |

*Primary Examiner*—John D. Yasko
*Attorney, Agent, or Firm*—Max Goldman

[57] ABSTRACT

A safety syringe uses a flexible, compressed, elastomeric O-ring to frictionally hold a needle holder with a needle in place. After use, the safety syringe is placed in a receptacle in the lid of a needle discard container and the plunger further depressed to release the needle holder and needle, which are then ejected into a discard container for safe and effective discarding of used needles. The discard procedure is accomplished using one hand and the needle is separated from the rest of the syringe to prevent re-use.

16 Claims, 2 Drawing Sheets

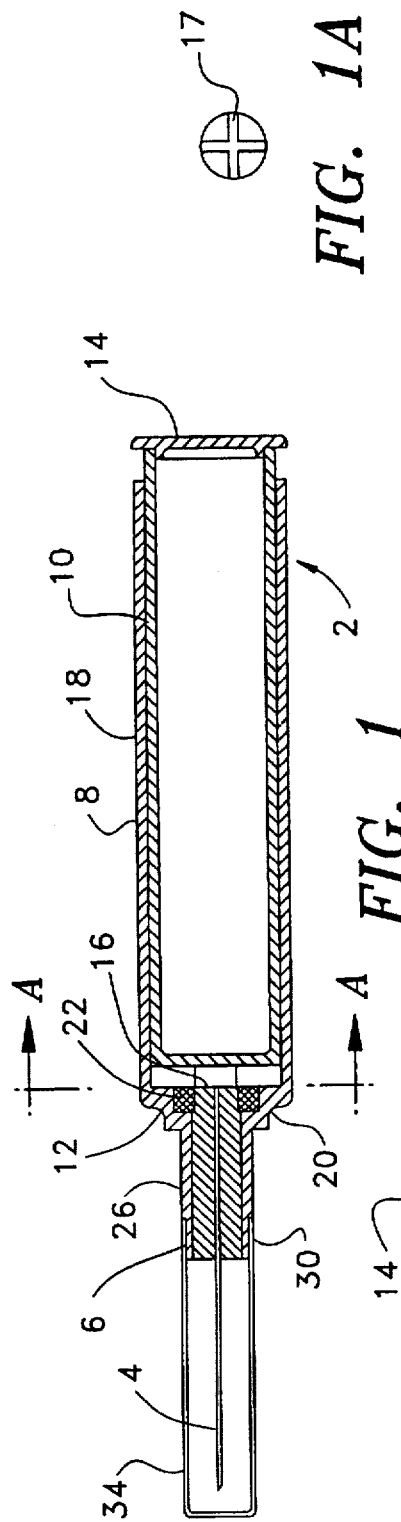
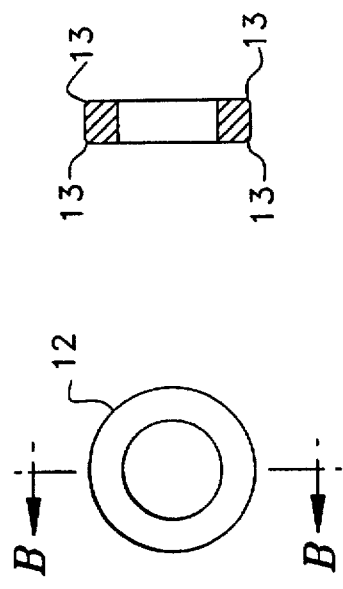
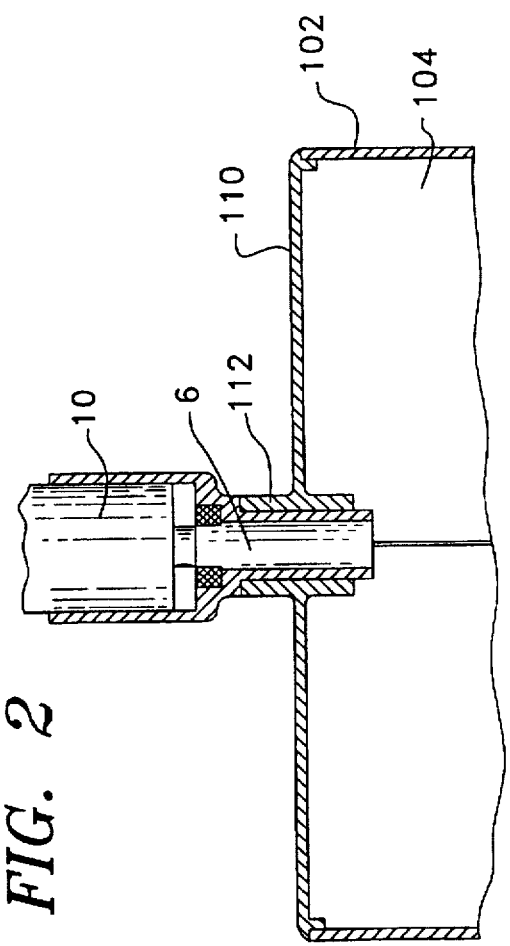

SAFETY SYRINGE SYSTEM

BACKGROUND OF THE INVENTION

This invention relates generally to syringes or hypodermic needles and more specifically to syringes employing a safe and effective means of discard of the needle after use. A major problem in the use of syringes and hypodermic needles relates to the safe and effective disposal of the needles after use. There is a danger that medical personnel and others who use the syringe can be inadvertently stuck or scratched by the needle after use. This can convey diseases and infections to such personnel. Also, a used syringe may be reused, possibly infecting another person.

Various means have been employed to provide safe use and disposal of hypodermic needles. For example, Shaw, Pat. No. 5,385,551, discloses a capped needle. When the cap is removed, a medical vial is punctured by the needle and plunger action draws the medicine into the syringe. The needle is then injected into a patient and the plunger moves forward to force the medicine into the patient's body.

During injection of the medicine, the needle which is held in place in a needle holder, is held in position through friction. After the injection is completed and the needle is removed from the patient, the plunger is forced forward releasing the frictional hold on the needle holder. The needle holder and needle are then retracted by the action of a spring, which was compressed during injection, and which is then released forcing the needle back into the body of the syringe. A potential problem with this device, in addition to the complexity and number of parts required, is that the syringe and needle can be used again because the needle is still available within the syringe.

Another type of safety device is disclosed by Columbus, et al. in U.S. Pat. No. 5,193,552. In this device, the needle moves in and out of a protective housing, between two operative positions, one of which causes the housing to shield the needle. Each operative position includes releasable locking detents that temporarily hold the needle in one of these positions. A third position is used to permanently lock the needle in position against accidental reuse.

A third type of safety device consists of a shield which surrounds the needle after its use and locks the needle into place. This requires the use of two hands and can result in accidental sticking during its application.

There is a need for a safety syringe which prevents the accidental sticking of medical personnel during use and disposal of the needle, which employs a minimal number of parts, is easy to manufacture, assemble and use and which prevents its reuse.

OBJECTS OF THE INVENTION

Accordingly, it is the general object of the instant invention to provide a safety syringe which improves upon and overcomes the shortcomings of present devices.

It is a further object of the instant invention to provide a safety syringe with a simple means for releasing the needle holder and needle from the syringe after use.

It is yet a further object of the instant invention to provide a safety syringe with a container into which used needles are discarded for safe disposal of the needles.

It is still yet a further object of the instant invention to provide a safety syringe which prevents reuse of hypodermic needles by separating the needle from the remainder of the syringe after use.

It is yet another object of the instant invention to provide a safety syringe which employs an elastomeric O-ring for retaining the needle holder or needle in position during use and for releasing the needle after its use.

It is still another object of the instant invention to provide a safety syringe which uses a minimum number of parts, and is easy to manufacture and assemble.

It is still yet another object of the instant invention to provide a safety syringe wherein used needles may be discarded using one hand.

SUMMARY OF THE INVENTION

These and other objects of the instant invention are achieved by providing a safety syringe with a container for disposal of used needles. The syringe employs a plunger to extract a medicine from a vial. Retraction of the plunger creates a vacuum which draws the medicine into the syringe. The needle is then inserted into a patient and the plunger brought forward to a stop position to inject the fluid in the plunger into the body of the patient.

During the application of the syringe, the needle holder and needle are frictionally held in position by a flexible, compressed, elastomeric O-ring.

After the fluid has been injected, the needle is removed from the patient and placed into a receptacle in the lid of a discard container. The plunger is then brought forward, past its stop position. A hub on the tip of the plunger releases the needle holder, with its needle, from the fricitional hold. The fluid remaining in the syringe cylinder forces the needle holder and needle to be deposited into the container. The syringe, minus its needle, is removed from the container receptacle. The container is then capped for additional safety.

DESCRIPTION OF THE DRAWINGS

Other objects and many of the intended advantages of this invention will be readily appreciated when the same becomes better understood by reference to the following detailed description, when considered in connection with the accompanying drawings, wherein:

FIG. 1 is a side sectional view of the safety syringe;

FIG. 1A is an end view of the nub at the end of the plunger 10, taken along the line A—A of FIG. 1;

FIG. 1B an end view of the O-ring of the safety syringe;

FIG. 1C is a sectional view of the O-ring taken along the line B—B of FIG. 1B.

FIG. 2 is a side view, in section of the safety syringe placed on a discard container for disposal of the needle holder and needle after use;

DETAILED DESCRIPTION OF THE PREFERRED EMBODIMENT

Figure 3:
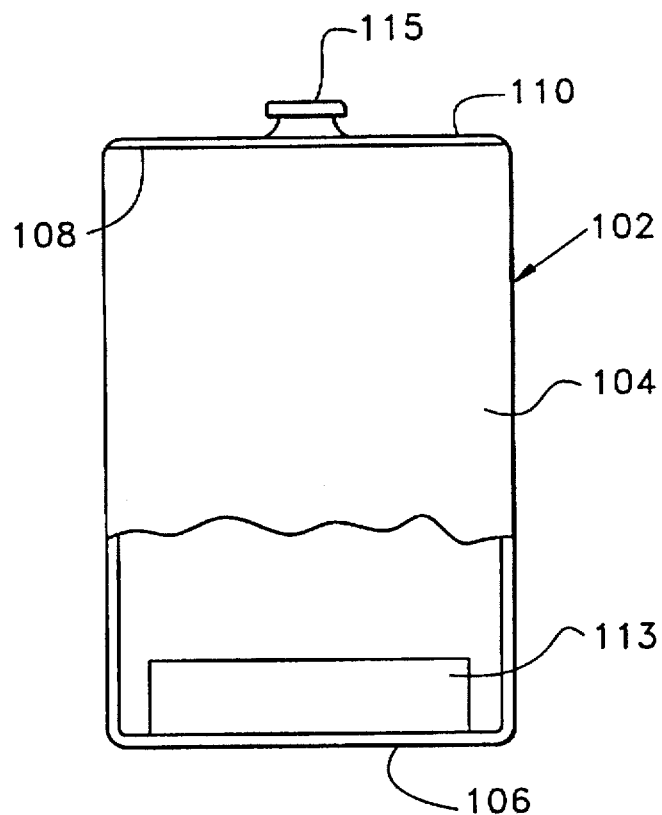
FIG. 3 is a side view of the needle discard container.

Referring now in greater detail to the various figures of the drawing, wherein like reference characters refer to like parts, there is shown in FIG. 1 the safety syringe of the instant invention. Safety syringe 2 comprises a needle 4, held in position within a needle holder 6 and a tube 8,in which the needle holder 6 is placed. The safety syringe 2 also comprises a plunger 10 with a cap 14. The plunger 10 is slidingly fitted in the tube 8.

The tube 8 includes a body section 18 and a second section 20. The safety syringe 2 also has an elastomeric O-ring 12 in contact with an inner surface 22 of the second section 20. The O-ring 12 is also in contact with the needle holder 6 and frictionally holds the needle holder in place. An an indented end section 30 of the tube 8 forms a seat upon which a cover 34 is placed over the needle 4 prior to use.

FIG. 1A shows a nub 16, at the tip of the plunger 10, which has a cross-cut 17 to allow the flow of any residual liquid from the safety syringe 2 after use of the syringe. This flow occurs as the needle 4 and needle holder 6 are discarded as the plunger 10 is moved past its first stop to its final stop.

FIG. 1B shows an end section of the O-ring 12. As can be seen in FIG. 1C which is a sectional view of the O-ring, the O-ring 12 has a square or rectangular shape with slightly rounded outer corners 13.

The purpose of making the O-ring square is to prevent rolling which would otherwise occur when round O-rings are subjected to axial forces. The slight rounding of the corners 13 of the O-ring 12 makes it easier to seat the O-ring during assembly of the safety syringe 2.

The O-ring 12 is made of an elastomeric material in order to provide a high coefficient of friction and to provide wide tolerances in the outside and inside diameters while closely controlling the induced radial pressure. The square cross-section also provides a large contact surface,which allows for a large friction force for a given pressure. Finally, as mentioned above,the square shape prevents rolling when axial forces are applied to the O-ring.

Figure 4:
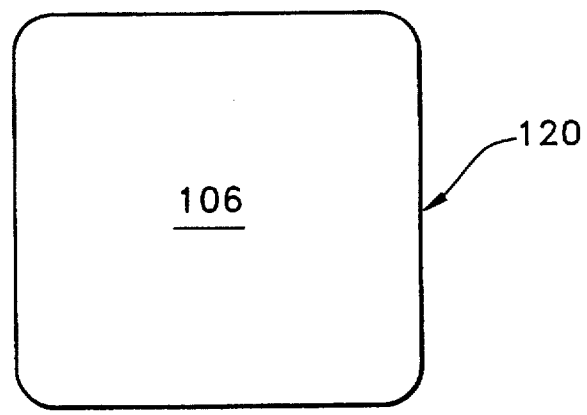
FIG. 4 is a bottom view of the needle discard container.

FIGS. 2,3 and 4 show a needle discard container 102 used in conjunction with the safety syringe 2. As can be seen in the Figs., the needle discard container 102 comprises a body section 104, a bottom 106 and a lid 110, which is permanently fastened to the body section 104. The lid 110 has a recepacle 112 which allows for the used needle holders and needles, to be ejected and to be stored and disposed of. Because a certain amount of fluid is released with the needle holders and needles, a sponge material 113 is placed at the bottom of the needle discard container 102.

FIG. 4 shows a bottom view of the needle discard container 102 showing its square or rectangular form. This shape increases its capacity for holding used needles.

The use of the device will now be explained. The cap 34 is first removed manually and the needle is inserted into a medicine vial containing the fluid to be injected into the patient. The plunger 10 is retracted by pulling on the cap 14 creating a vacuum and drawing the fluid from the medicine vial into the tube 8 of the safety syringe 2. The needle is then injected into the patient and the plunger 10 is moved forward to its first stop position by pressing on the cap 14 until the fluid in the safety syringe 2 is forced from the tube 8 through the needle 4 into the patient.

The needle is then removed from the patient and the safety syringe 2 is placed needle down in the receptacle 112 of the lid 108. The hub 16 at the end of the plunger 10 is in contact with the needle holder 6. Further depression of the plunger 10 to its final stop position moves the needle holder out of contact with the O-ring and forces the remaining fluid out of the syringe body. Releae from the O-ring and the fluid flow ejects the needle into the container 102. When the discard container is not in use, or is full, a cap 115 is placed on the receptacle 112 for further safety.

A safety syringe using a compressed, flexible elastomeric O-ring to frictionally hold the needle holder and needle in place during use has been described. After use, the needle and needle holder are released by further action of the plunger and drop into a discard container which holds a plurality of needle holders and needles, for safe and effective disposal.

Without elaboration, the foregoing will so fully illustrate my invention, that others may, by applying current or future knowledge, readily adapt the same for use under the various conditions of service.

I claim:

1. A syringe system for injecting a fluid into the body comprising:

(a) A tube having a body section and a second section with a seat at said second section;

(b) A plunger slidingly positioned in said tube with a distal end and a proximal end and a cap fastened to said proximal end;

(c) A needle holder slidingly located within said tube at said second section and holding a needle;

(d) An elastomeric O-ring located in said seat and in contact with said needle holder to frictionally hold said needle holder with said needle within said tube at said second section during injection of said fluid;

(e) Means for forcibly ejecting said needle holder from the frictional hold of said O-ring and separating said needle holder from said tube,using one hand and;

(f) A discard container for storage and disposal of said needle holder and needle after use.

2. The syringe system of claim 1 wherein said tube further comprises an end section with a second seat thereon to hold a needle cover prior to use of said syringe.

3. The syringe system of claim 2 wherein said plunger comprises a hub formed at said distal end.

4. The syringe system of claim 3 wherein said nub comprises a cross-cut for releasing the fluid remaining in said tube after use of said syringe and during needle ejection.

5. The syringe system of claim 4 wherein said needle holder comprises a second distal end and a second proximal end with said needle holder in frictional contact with the said O-ring at said second proximal end.

6. The syringe system of claim 1 wherein said means for forcibly ejecting said needle holder from the frictional hold of said O-ring comprises a nub at said distal end of said plunger which pushes against said needle holder, when pressure is applied to said cap.

7. The syringe system of claim 1 wherein said discard container comprises a second body section, a bottom and a lid with a receptacle to receive said syringe after its use.

8. The syringe system of claim 7 wherein said container is hollow with a square cross-section and further comprises a sponge material for absorbing fluids which accrue in said container with said discarded needles.

9. The syringe system of claim 6 wherein said tube further comprises an end section with a second seat thereon to hold a needle cover prior to use of said syringe.

10. The syringe system of claim 8 wherein said tube further comprises an end section with a second seat thereon to hold a needle cover prior to use of said syringe.

11. The syringe system of claim 10 wherein said plunger comprises a nub formed at said distal end.

12. The syringe system of claim 11 wherein said nub comprises a cross-cut for releasing the fluid remaining in said tube after use of said syringe.

13. The syringe system of claim 12 wherein said needle holder comprises a second proximal end and a second distal end with said needle holder in frictional contact with said O-ring at said second proximal end.

14. The syringe system of claim 7 wherein said O-ring has a cross section in the shape of a square with outer corners.

15. The syringe system claim 14 wherein the outer corners of said square are rounded.

16. A syringe for inserting a fluid into the body comprising;
   (a) A tube having a body section and a second section with a seat at said second section;
   (b) A plunger slidingly positioned in said tube with a distal end and a proximal end and a cap fastened at said second proximal end;
   (c) A needle holder slidingly located within said tube at said second section and holding a needle;
   (d) An elastomeric O-ring located in said seat and in contact with said needle holder to frictionally hold said needle holder, with said needle, within said tube at said second section during injection of the fluid; and
   (e) Means for forcibly ejecting from the frictional hold of said O-ring and separating said needle holder from said tube, using one hand.

* * * * *